(12) United States Patent
Ninomiya et al.

(10) Patent No.: US 7,650,994 B2
(45) Date of Patent: Jan. 26, 2010

(54) ADHESIVE PREPARATION PACKAGE

(75) Inventors: Kazuhisa Ninomiya, Ibaraki (JP); Shoji Goshima, Ibaraki (JP)

(73) Assignee: Nitto Denko Corporation, Ibaraki (JP)

( * ) Notice: Subject to any disclaimer, the term of this patent is extended or adjusted under 35 U.S.C. 154(b) by 366 days.

(21) Appl. No.: 11/169,530

(22) Filed: Jun. 29, 2005

(65) Prior Publication Data

US 2006/0000734 A1    Jan. 5, 2006

(30) Foreign Application Priority Data

Jul. 1, 2004    (JP)    ............................. 2004-195321
Jun. 13, 2005    (JP)    ............................. 2005-172516

(51) Int. Cl.
*A61B 19/02*    (2006.01)
*B65D 73/00*    (2006.01)
*B65D 65/26*    (2006.01)

(52) U.S. Cl. ........................ 206/438; 206/484; 383/210

(58) Field of Classification Search ......... 206/438–440, 206/484, 484.1, 484.2, 460, 210, 570, 828; 383/210, 211
See application file for complete search history.

(56) References Cited

U.S. PATENT DOCUMENTS

| | | | |
|---|---|---|---|
| 2,069,335 A | | 2/1937 | Salfisberg |
| 3,552,638 A | * | 1/1971 | Quackenbush .............. 383/210 |
| 3,913,789 A | * | 10/1975 | Miller ......................... 206/484 |
| 4,058,632 A | * | 11/1977 | Evans et al. ................. 383/210 |
| 5,181,610 A | * | 1/1993 | Quick et al. ................. 206/447 |
| 5,505,306 A | | 4/1996 | Akemi et al. |
| 5,950,830 A | * | 9/1999 | Trigger ....................... 206/440 |

FOREIGN PATENT DOCUMENTS

| | | |
|---|---|---|
| BE | 423 191 A | 9/1937 |
| DE | 92 09 137.7 U1 | 9/1992 |
| EP | 1 045 656 B1 | 1/2003 |

* cited by examiner

*Primary Examiner*—J. Gregory Pickett
(74) *Attorney, Agent, or Firm*—Leydig, Voit & Mayer, Ltd.

(57) ABSTRACT

The present invention provides an adhesive preparation package containing an adhesive preparation and a packaging film (s) enclosing said preparation, the packaging films being heat-sealed around the adhesive preparation, wherein the heat-sealed portion of the packaging film comprises an embossed heat-sealed portion and a flat heat-sealed portion, and the embossed heat-sealed portion and the flat heat-sealed portion each form a pattern surrounding the periphery of the adhesive preparation. The adhesive preparation package of the present invention is free of occurrence of pinholes in a heat-sealed portion and can maintain superior air-tightness and sterility.

11 Claims, 4 Drawing Sheets

ADHESIVE PREPARATION PACKAGE

FIELD OF THE INVENTION

The present invention relates to an adhesive preparation package. More particularly, the present invention relates to an adhesive preparation package comprising an adhesive preparation enclosed in a packaging film(s) heat-sealed around the adhesive preparation.

BACKGROUND OF THE INVENTION

In recent years, for the protection and cure of wound, bedsore, burn ulcer, donor site and the like of human skin, dressing agents having various functions have been developed. Dressing agents are individually packaged and then sterilized to prevent the skin from being infected with bacteria. This packaging has an important role of ensuring high sterility.

As a means of administering a drug to living organisms, a method for transdermal absorption of the drug through the skin, which comprises adhering an adhesive preparation containing a drug to a living organism, has been developed. Such a drug-containing adhesive preparation comprises a support made of a plastic film of polyester, polyethylene and the like, or a non-woven fabric, and an adhesive layer containing a transdermally absorbable drug, which is laminated on one surface of the support, wherein the exposed surface of the adhesive layer is covered with a coating material. Generally, such a drug-containing adhesive preparation is individually packaged with a packaging film for the purpose of preventing volatilization of the contained drug and/or influence of humidity, oxygen and the like (decomposition, oxidation and the like).

In general, individual packaging is performed by heat-sealing the packaging film surrounding the adhesive preparation by a packaging machine.

For the packaging film, various films impermeable or hardly permeable to humidity and oxygen have been developed. Depending on the kind of the packaging film and packaging methods, however, the heat-sealing treatment may not be sufficient, and a pinhole sometimes occurs. Occurrence of pinholes in the heat-sealed portion includes such occurrence due to an excessive pressure and heat applied for heat blocking for a heat sealing treatment, which causes breakage of a part of a packaging film, such occurrence due to an insufficient pressure and heat for the heat block, which makes the heat sealing treatment incomplete to allow pinholes, such occurrence due to wrinkles in the heat-sealed portion and the like. Moreover, since packaging films have inconsistent thicknesses, which in turn causes variation in the heat-sealing pressure on the heat-sealed portion, an effect of the tension on the packaging film becomes greater to permit easy development of the wrinkles. As a result, a pinhole easily occurs.

The band width of the heat-sealed portion is conventionally about 3 mm to 8 mm or above. To perform a heat sealing treatment free of occurrence of a pinhole by simultaneously and uniformly pressing a packaging film, while forming a heat-sealed portion with such a band width, control of special machines, determination of material and thickness of the packaging film and the like were necessary. Particularly, determination of the material and thickness of the packaging film is essential for avoiding the occurrence of pinholes. For packaging without a pinhole, a heat sealing resin capable of adhering at a low temperature is often used as a material of a packaging film, and in this case, the thickness of a packaging film tends to be greater.

When a transdermal absorption type adhesive preparation containing a drug is packaged, since the drug adsorbs to a heat sealable resin during preservation, the drug content of the adhesive preparation decreases, thus affecting the treatment effect. As a material of the packaging film, therefore, a heat sealable resin hardly adsorbable for drugs needs to be used. Moreover, to reduce the amount of the drug adsorbed to the packaging film as a whole, the thickness also needs to be made small. A heat sealable resin hardly adsorbable for drugs tends to require a higher heat sealing treatment temperature. In addition, when the thickness of the packaging film is reduced, the pressure for the heat sealing treatment tends to be non-uniformly applied to the entire portion of a packaging film to be heat sealing-treated. As a result, a pinhole easily occurs.

Conventionally, as the above-mentioned heat-sealed portion, an embossed heat-sealed portion (heat-sealed portion having a pattern of concave-convex, for example, tatami-matting weave-like dots, lattice and the like) has been employed. Therefore, minute pinholes are difficult to find by a nondestructive test such as an appearance test and the like. Accordingly, minute pinholes can only be found by a method including destruction of heat-sealed portion and the like, and the method is also problematic in view of the assurance of quality.

SUMMARY OF THE INVENTION

The present invention aims at solving the above-mentioned problems and provides an adhesive preparation package free of pinholes in a heat-sealed portion, which can easily achieve air-tightness and sterility.

The present inventors have conducted intensive studies in an attempt to solve the above-mentioned problems and found that pinholes in a heat-sealed portion can be avoided by an adhesive preparation package comprising an adhesive preparation and packaging films sandwiching said preparation, the packaging films being heat-sealed around the adhesive preparation, wherein the heat-sealed portion of the packaging films comprises an embossed heat-sealed portion and a flat heat-sealed portion, and the embossed heat-sealed portion and the flat heat-sealed portion form a pattern surrounding the periphery of the adhesive preparation. As a result of the additional detailed study, they have found that pinholes in a heat-sealed portion can be certainly avoided by such adhesive preparation package, wherein the embossed heat-sealed portion and the flat heat-sealed portion each form a pattern concentrically surrounding the periphery of the adhesive preparation and the flat heat-sealed portion has a band width of 0.4 mm to 2.0 mm, which resulted in the completion of the present invention. In addition, they have found that, when a transparent packaging film is used, the presence of pinholes in a flat heat-sealed portion can be determined by a visual test or image treatment test. Accordingly, the present invention provides the following.

[1] An adhesive preparation package comprising an adhesive preparation and a packaging film(s) enclosing said preparation, the packaging films being heat-sealed around the adhesive preparation, wherein the heat-sealed portion of the packaging film comprises an embossed heat-sealed portion and a flat heat-sealed portion, and the embossed heat-sealed portion and the flat heat-sealed portion each form a pattern surrounding the periphery of the adhesive preparation.

[2] The adhesive preparation package of the above-mentioned [1], wherein the flat heat-sealed portion has a band width of 0.4 mm to 2.0 mm.

[3] The adhesive preparation package of the above-mentioned [1] or [2], wherein the embossed heat-sealed portion and the flat heat-sealed portion each form a pattern concentrically surrounding the periphery of the adhesive preparation.

[4] The adhesive preparation package of any of the above-mentioned [1] to [3], wherein the embossed heat-sealed portion and the flat heat-sealed portion form a pattern surrounding the periphery of the adhesive preparation, which pattern consisting of a combination of (1) a flat heat-sealed portion and an embossed heat-sealed portion, (2) an embossed heat-sealed portion and a flat heat-sealed portion, (3) an embossed heat-sealed portion, a flat heat-sealed portion and an embossed heat-sealed portion, and (4) a flat heat-sealed portion, an embossed heat-sealed portion and a flat heat-sealed portion in the order from the inside.

[5] The adhesive preparation package of any of the above-mentioned [1] to [4], wherein the heat-sealed portion of the packaging film(s) has a total band width of 3 mm to 20 mm for the combination of the embossed heat-sealed portion and the flat heat-sealed portion.

[6] The adhesive preparation package of any of the above-mentioned [1] to [5], wherein the adhesive preparation is sandwiched between two packaging films, and the packaging films around the periphery of the adhesive preparation are heat-sealed.

[7] The adhesive preparation package of any of the above-mentioned [1] to [6], wherein the adhesive preparation has a thickness of 50 μm to 2000 μm.

[8] The adhesive preparation package of any of the above-mentioned [1] to [7], wherein the adhesive preparation comprises an adhesive layer, a support laminated on one surface of the adhesive layer and a peel-treated release liner laminated on the other surface of the adhesive layer.

[9] The adhesive preparation package of the above-mentioned [8], wherein the adhesive layer comprises a transdermally absorbable drug.

[10] The adhesive preparation package of any of the above-mentioned [1] to [9], wherein the packaging film comprises a base film layer and a thermally adhesive resin layer having a thickness of 3 μm to 40 μm is laminated.

[11] The adhesive preparation package of the above-mentioned [10], wherein the resin constituting the thermally adhesive resin layer is a polyacrylonitrile resin or a polyolefin resin.

[12] The adhesive preparation package of any of the above-mentioned [1] to [11], wherein the packaging film is transparent.

[13] An adhesive preparation package comprising an adhesive preparation and packaging films sandwiching said preparation, the packaging films being heat-sealed around the adhesive preparation, wherein the heat-sealed portion of the packaging film comprises an embossed heat-sealed portion and a flat heat-sealed portion, the embossed heat-sealed portion and the flat heat-sealed portion each form a pattern concentrically surrounding the periphery of the adhesive preparation, and the flat heat-sealed portion has a band width of 0.4 mm to 2.0 mm.

[14] The adhesive preparation package of the above-mentioned [13], wherein the embossed heat-sealed portion and the flat heat-sealed portion form a concentric pattern consisting of a combination of (1) a flat heat-sealed portion and an embossed heat-sealed portion, (2) an embossed heat-sealed portion and a flat heat-sealed portion, (3) an embossed heat-sealed portion, a flat heat-sealed portion and an embossed heat-sealed portion, or (4) a flat heat-sealed portion, an embossed heat-sealed portion and a flat heat-sealed portion in the order from the inside.

[15] The adhesive preparation package of the above-mentioned [13] or [14], wherein the heat-sealed portion of the packaging film has a total band width of 3 mm to 20 mm for the combination of the embossed heat-sealed portion and the flat heat-sealed portion.

[16] The adhesive preparation package of any of the above-mentioned [13] to [15], wherein the adhesive preparation is sandwiched between two packaging films, and the packaging film around the periphery of the adhesive preparation is heat-sealed.

[17] The adhesive preparation package of any of the above-mentioned [13] to [16], wherein the adhesive preparation has a thickness of 50 μm to 2000 μm.

[18] The adhesive preparation package of any of the above-mentioned [13] to [17], wherein the adhesive preparation comprises an adhesive layer, a support laminated on one surface of the adhesive layer and a peel-treated release liner laminated on the other surface of the adhesive layer.

[19] The adhesive preparation package of the above-mentioned [18], wherein the adhesive layer comprises a transdermally absorbable drug.

[20] The adhesive preparation package of any of the above-mentioned [13] to [19], wherein the packaging film comprises a base film layer and a thermally adhesive resin layer having a thickness of 3 μm to 40 μm is laminated.

[21] The adhesive preparation package of the above-mentioned [20], wherein the resin constituting the thermally adhesive resin layer is a polyacrylonitrile resin or a polyolefin resin.

[22] The adhesive preparation package of any of the above-mentioned [13] to [21], wherein the packaging film is transparent.

Figure 1:
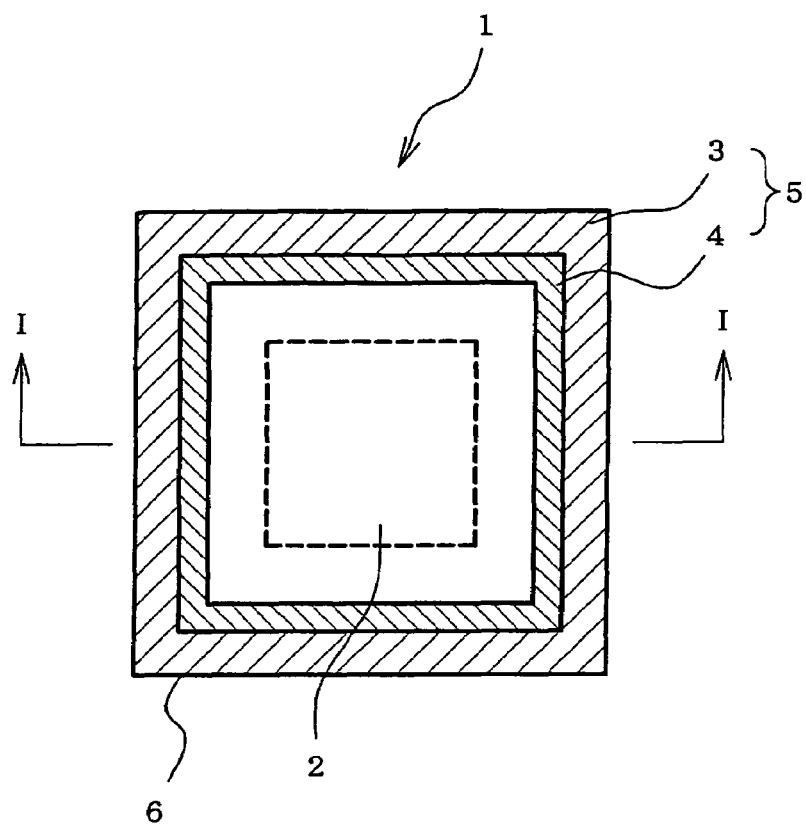
FIG. 1 is a plan view of one embodiment of the adhesive preparation package of the present invention, wherein the hatching has been applied to show the boundary between an embossed heat-sealed portion 3 and a flat heat-sealed portion 4.

In the Figures, 1 shows an adhesive preparation package, 2 shows an adhesive preparation, 3 shows an embossed heat-sealed portion, 4 shows a flat heat-sealed portion, 5 shows a heat-sealed portion and 6 shows a packaging film.

EFFECT OF THE INVENTION

In the adhesive preparation package of the present invention, for example, a medical adhesive preparation for a treatment is completely sealed (enclosed) without wrinkles or pinholes by a heat sealing treatment. In other words, the adhesive preparation package of the present invention comprises an adhesive preparation and packaging films sandwiching said preparation, the packaging films being heat-sealed around the periphery of the adhesive preparation, wherein the heat-sealed portion of the packaging film comprises an embossed heat-sealed portion and a flat heat-sealed portion, and the embossed heat-sealed portion and the flat heat-sealed portion form a pattern surrounding the periphery of the adhesive preparation, whereby the heat-sealed portion becomes free of occurrence of a pinhole, and air-tightness and sterility can be maintained easily. By such adhesive preparation package, wherein the embossed heat-sealed portion and the flat heat-sealed portion each form a pattern concentrically surrounding the periphery of the adhesive preparation and the flat heat-sealed portion has a band width of 0.4 mm to 2.0 mm, the heat-sealed portion becomes free of occurrence of a pinhole, and air-tightness and sterility can be maintained more easily. Therefore, when an adhesive preparation containing a drug susceptible to oxidation due to oxygen and decomposition due to moisture is packaged, the adhesive preparation package of the present invention can act as a deoxidizer or a moisture remover, and oxidation and decomposition can be greatly suppressed. When a dressing agent and the like are packaged as an adhesive preparation, sterility can be highly ensured. Moreover, since the adhesive preparation package of the present invention is essentially free of wrinkles in the heat-sealed portion, it has a good appearance and high value as a product. When a transparent packaging film is used, a visual test of the flat sealed portion permits confirmation of the absence of chap in the flat sealed portion and complete heat sealing (enclosure). Instead of this visual test, images of a flat heat-sealed portion may be taken into a camera, which are then image treated by, for example, a binary treatment, whereby the absence of chap in the flat heat-sealed portion can be confirmed by an automatic detection.

In the adhesive preparation package of the present invention, moreover, since the thickness of a thermally adhesive resin layer consisting a packaging film can be made small, when the adhesive preparation contains a drug, adsorption of the drug to the thermally adhesive resin layer can be reduced and a package containing an adhesive preparation capable of exhibiting a stable treatment effect can be provided.

BEST MODE FOR CARRYING OUT THE INVENTION

The present invention is explained in detail in the following.

The adhesive preparation package of the present invention comprises an adhesive preparation and packaging films sandwiching said preparation, the packaging films being heat-sealed around the periphery of the adhesive preparation, wherein the heat-sealed portion of the packaging film (hereinafter to be also referred to as a heat-sealed portion) comprises an embossed heat-sealed portion and a flat heat-sealed portion, and the embossed heat-sealed portion and the flat heat-sealed portion each form a pattern surrounding the periphery of the adhesive preparation. Particularly, the adhesive preparation package which comprises an adhesive preparation and packaging films sandwiching said preparation, the packaging films being heat-sealed around the periphery of the adhesive preparation, wherein the heat-sealed portion comprises an embossed heat-sealed portion and a flat heat-sealed portion, the embossed heat-sealed portion and the flat heat-sealed portion each form a pattern concentrically surrounding the periphery of the adhesive preparation, and the flat heat-sealed portion has a band width of 0.4 mm to 2.0 mm is preferable.

In the present invention, by "the packaging film around the periphery of the adhesive preparation is heat-sealed" is meant that the packaging film around the periphery of the adhesive preparation has a heat-sealed portion formed to enclose the adhesive preparation. For example, when the adhesive preparation package is quadrangle and heat-sealed with an adhesive preparation sandwiched between two packaging films, a heat-sealed portion is formed on four sides of the packaging film so as to enclose the adhesive preparation. For example, when the adhesive preparation package is quadrangle and heat-sealed while sandwiching an adhesive preparation between two-folded pieces of one sheet of the packaging film, a heat-sealed portion is formed on three sides of the packaging film excluding the folded portion of the film.

In the present invention, by the concentrically of "a pattern concentrically surrounding the periphery of the adhesive preparation" is meant concentricity about the adhesive preparation.

Figure 5:
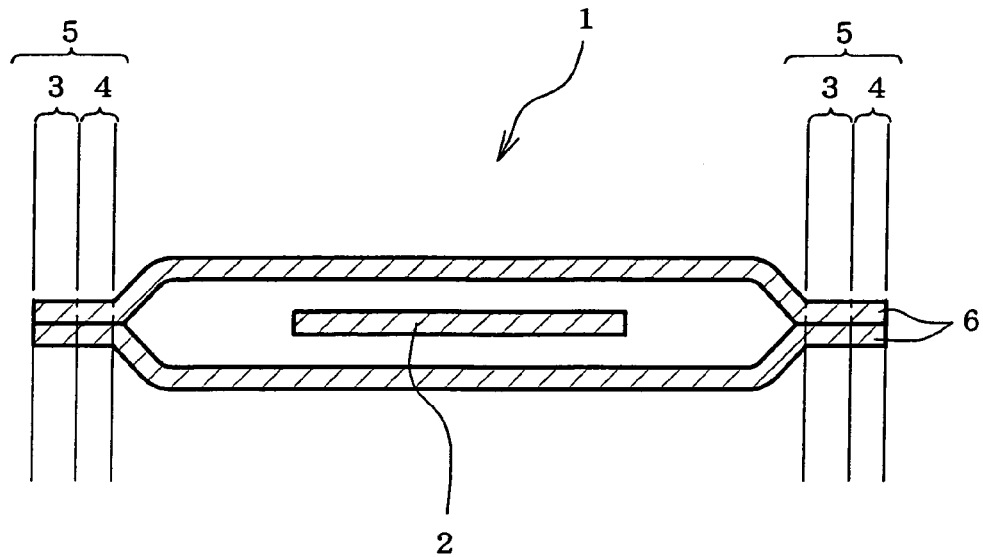
FIG. 5 is a sectional view of one embodiment of the adhesive preparation package of the present invention.

One embodiment of the adhesive preparation package of the present invention is shown in FIGS. 1 and 5. FIG. 1 is a plan view showing a quadrangle adhesive preparation package 1. FIG. 5 is a sectional view along the line I-I of the adhesive preparation package 1. In the present specification, the size ratios on the Figures do not always reflect the same measures, for the sake of convenience of the presentation. As shown in FIGS. 1 and 5, the adhesive preparation 2 is packaged (enclosed) with a packaging film 6. A heat-sealed portion 5 is formed around the adhesive preparation 2 by heat sealing the packaging film 6, and the heat-sealed portion 5 comprises a flat heat-sealed portion 3 and an embossed heat-sealed portion 4, which are respectively formed as patterns concentrically surrounding the adhesive preparation 2.

Figure 6:
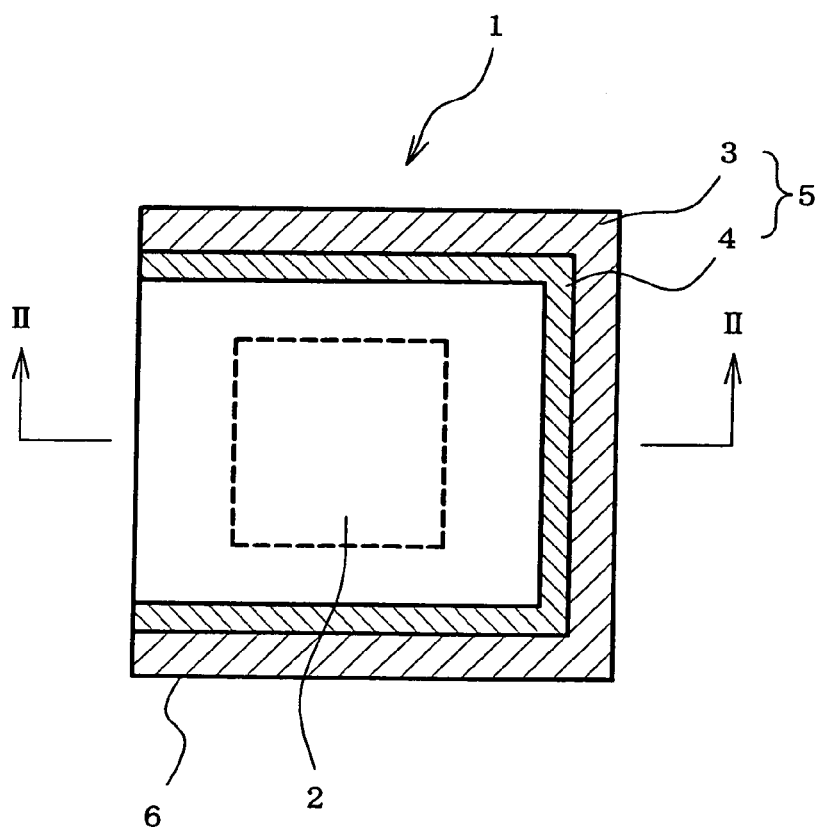
FIG. 6 is a plan view of another embodiment of the adhesive preparation package of the present invention, wherein the hatching has been applied to show the boundary between an embossed heat-sealed portion 3 and a flat heat-sealed portion 4.
Figure 7:
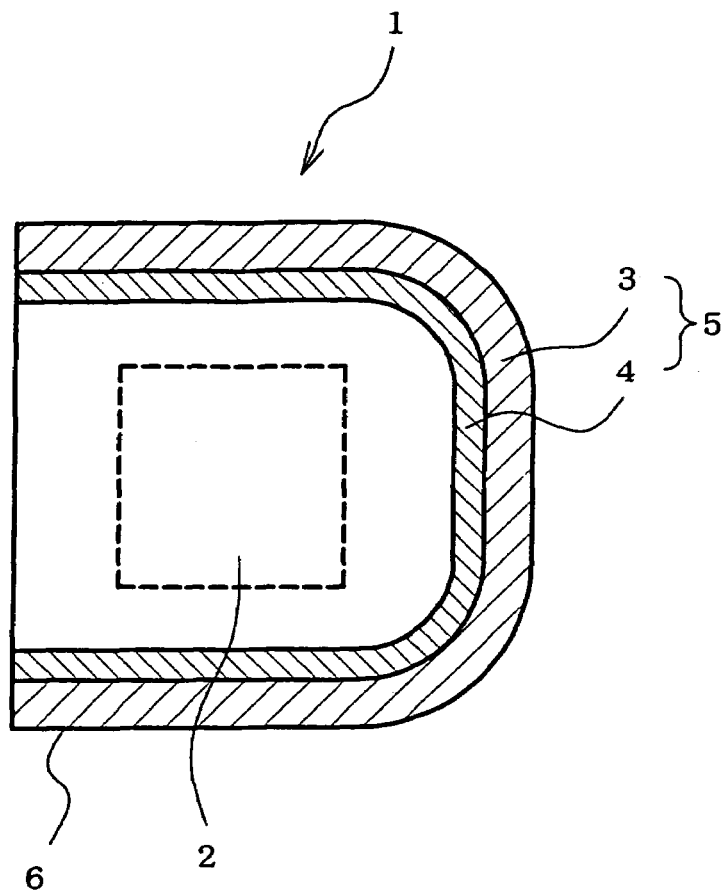
FIG. 7 is a plan view of another embodiment of the adhesive preparation package of the present invention, wherein the hatching has been applied to show the boundary between an embossed heat-sealed portion 3 and a flat heat-sealed portion 4.
Figure 8:
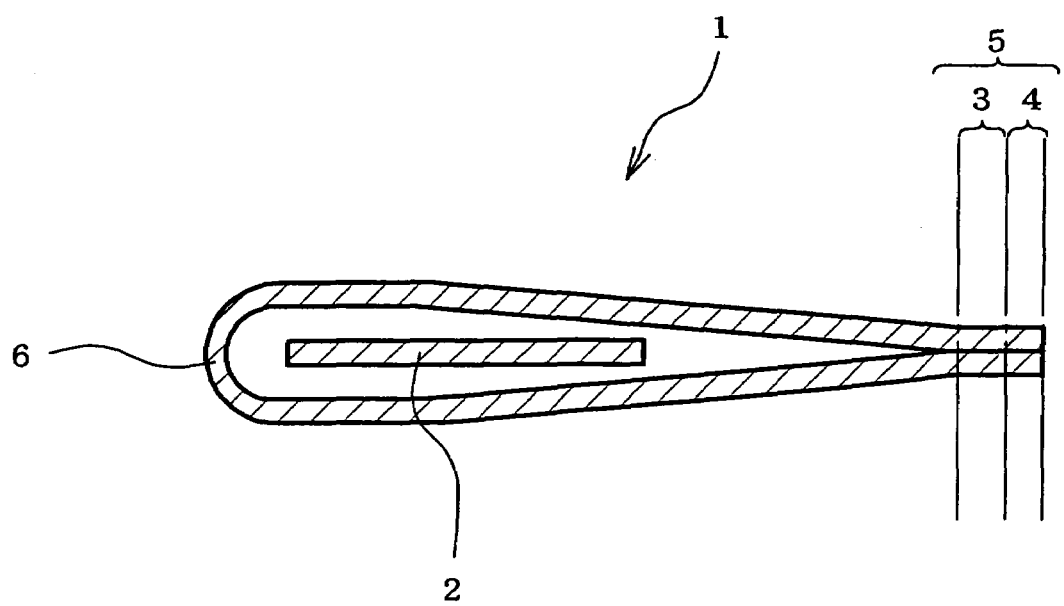
FIG. 8 is a sectional view of another embodiment of the adhesive preparation package of the present invention.

Other embodiments of the adhesive preparation package of the present invention are shown in FIGS. 6-8. FIG. 6 is a plan view showing a quadrangle adhesive preparation package 1, and FIG. 8 is a sectional view along the line II-II of the adhesive preparation package 1. As shown in FIGS. 6 and 8, the adhesive preparation 2 is packaged (enclosed) with a packaging film 6 folded in two. A heat-sealed portion 5 is formed on three sides of the packaging film excluding the folded portion of the packaging film 6. The heat-sealed portion 5 comprises a flat heat-sealed portion 3 and an embossed heat-sealed portion 4 each formed as a pattern surrounding the periphery of the adhesive preparation 2. The folded packaging film 6 may have a round corner as shown in FIG. 7.

The heat-sealed portion has a band width of preferably 3 mm to 20 mm, more preferably 4 to 8 mm, for the total of the embossed heat-sealed portion and the flat heat-sealed portion. When the band width is smaller than 3 mm, an appropriate sealing strength within the below-mentioned range cannot be obtained, and pinholes tend to occur. The band width greater than 20 mm is not economical. The sealing strength of the heat-sealed portion is preferably 1 to 30 N/15 mm, more preferably 3 to 20 N/15 mm, still more preferably 6 to 15 N/15 mm. When the sealing strength is smaller than 1 N/15 mm, the heat-sealed portion more frequently peels off and pinholes occur more often. The upper limit of the sealing strength is limited by breaking strength and stiffness of the below-mentioned thermally adhesive resin layer constituting the packaging film. In the present invention, the sealing strength is based on JIS Z0238, "Testing methods for heat-sealed flexible packages".

The embossed heat-sealed portion has concaves and convexes, and as the concaves and convexes, for example, conventional patterns such as tatami-matting weave-like dots, lattice, line, wave, dot and the like can be mentioned. To achieve an appropriate sealing strength within the above-mentioned range, a combination of tatami-matting weave-like dots and a line is preferable. The pitch of the above-mentioned pattern can be set, for example, within the range of 0.2 to 2 mm, preferably within the range of 0.4 to 0.8 mm, for tatami-matting weave-like dots. When the pitch of the tatami-matting weave-like dots is smaller than 0.2 mm, molding with a heat block metal becomes difficult during formation of an embossed heat-sealed portion, and when it is wider than 2 mm, pinholes tend to occur and the resulting package has poor appearance.

The flat heat-sealed portion is flat without concaves and convexes and the like. The band width of the flat sealed portion is 0.4 to 2.0 mm, preferably 0.5 to 1.0 mm, more preferably 0.5 to 0.7 mm. When the band width is narrower than 0.4 mm, the effect of prevention of pinholes becomes small, and when it is wider than 2.0 mm, the pressure for the heat sealing treatment is dispersed during the formation of the below-mentioned flat heat-sealed portion, which in turn makes the heat sealing treatment incomplete, sometimes allowing occurrence of pinholes, and air bubbles easily enter the flat heat-sealed portion, giving an unpreferable appearance.

Figure 2:
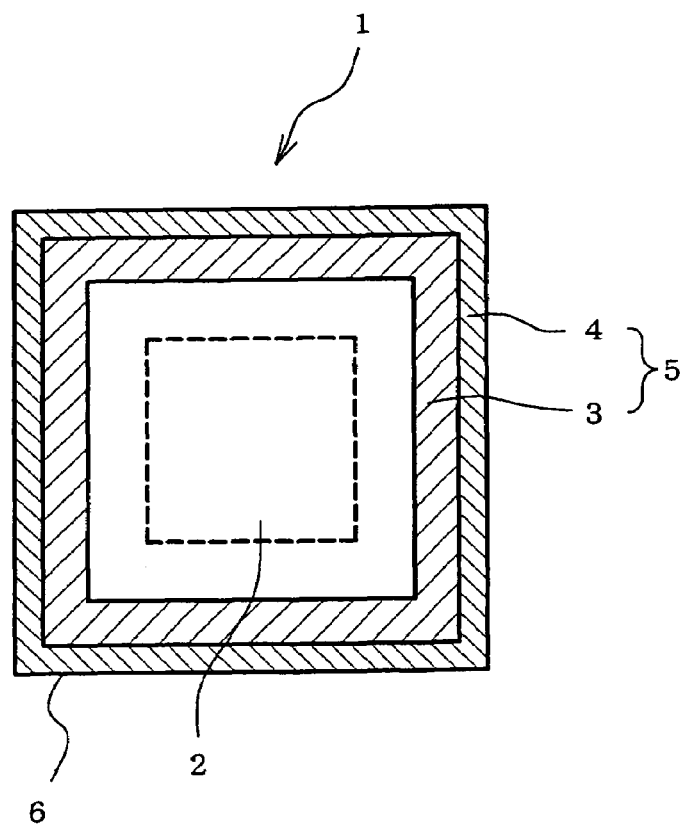
FIG. 2 is a plan view of another embodiment of the adhesive preparation package of the present invention, wherein the hatching has been applied to show the boundary between an embossed heat-sealed portion 3 and a flat heat-sealed portion 4.
Figure 3:
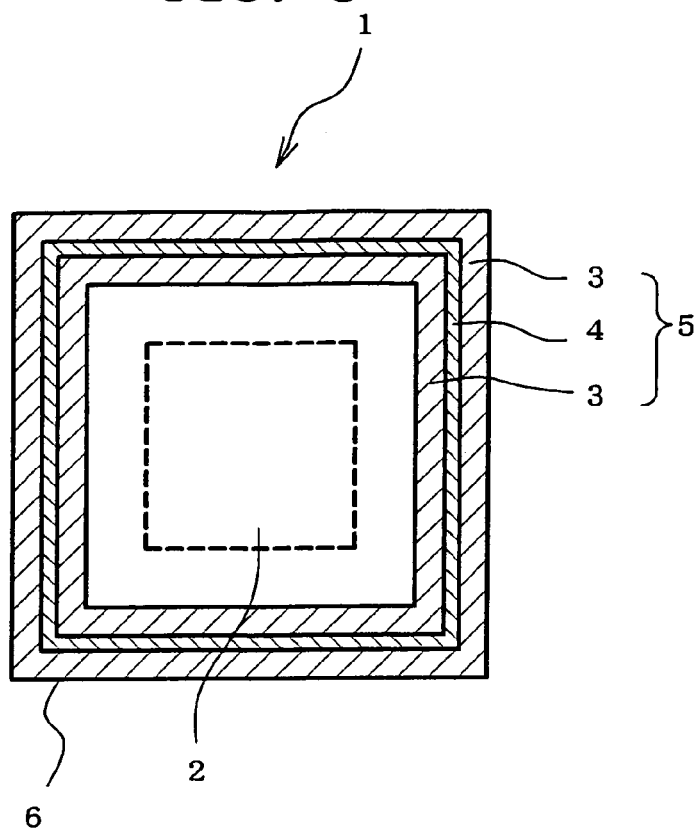
FIG. 3 is a plan view of another embodiment of the adhesive preparation package of the present invention, wherein the hatching has been applied to show the boundary between an embossed heat-sealed portion 3 and a flat heat-sealed portion 4.
Figure 4:
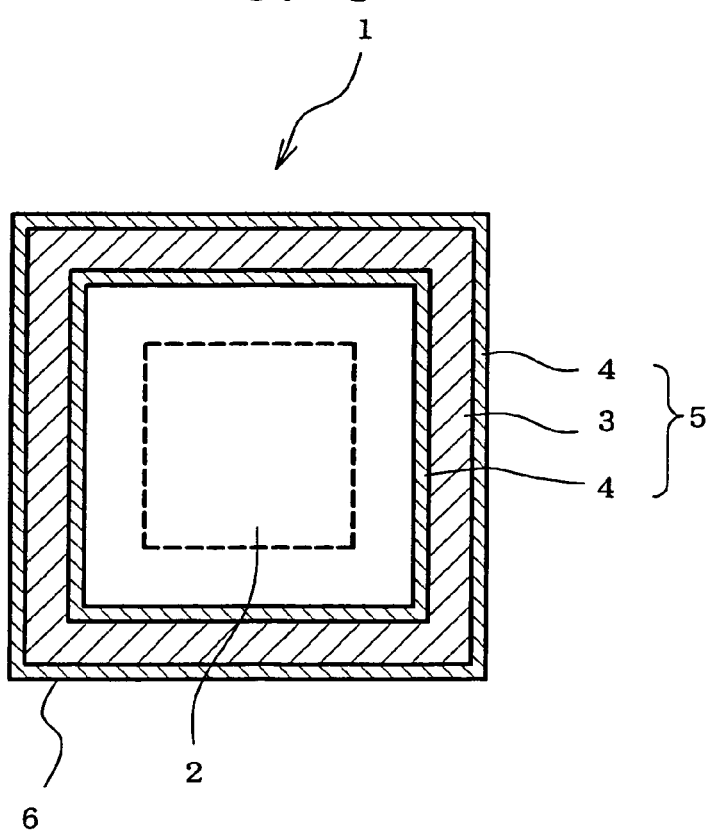
FIG. 4 is a plan view of another embodiment of the adhesive preparation package of the present invention, wherein the hatching has been applied to show the boundary between an embossed heat-sealed portion 3 and a flat heat-sealed portion 4.

While the concentric pattern formed by an embossed heat-sealed portion and a flat heat-sealed portion is not particularly limited, for example, the combinations of (1) a flat heat-sealed portion and an embossed heat-sealed portion (FIG. 1), (2) an embossed heat-sealed portion and a flat heat-sealed portion (FIG. 2), (3) an embossed heat-sealed portion, a flat heat-sealed portion and an embossed heat-sealed portion (FIG. 3) and (4) a flat heat-sealed portion, an embossed heat-sealed portion and a flat heat-sealed portion (FIG. 4) from the inside in these orders can be mentioned. Of these, the combination of (1) a flat heat-sealed portion and an embossed heat-sealed portion (FIG. 1) is preferable because a desired sealing strength can be easily obtained. When the pattern of an embossed heat-sealed portion and a flat heat-sealed portion is not concentric, the above-mentioned combinations (1) to (4) can be mentioned as the pattern, with preference given to (1).

In connection with the below-mentioned heat sealing treatment method, when plural flat heat-sealed portions are simultaneously formed, heat sealing treatment becomes incomplete because the heat sealing pressure is dispersed, and pinholes easily occur. Therefore, a single flat heat-sealed portion (e.g., embodiment shown in FIGS. 1 to 3, 6 and 7) is preferable, and formation of a single flat heat-sealed portion is sufficient to provide the action and effect of the present invention.

The shape of the adhesive preparation package of the present invention is not particularly limited as long as it can package an adhesive preparation. For example, quadrangle (square, rectangle and the like), polygonal (triangle and the like), circle, ellipse, other shape and the like can be mentioned. In addition, the shape of the adhesive preparation package and that of the adhesive preparation to be packaged may be the same or different as long as the adhesive preparation can be packaged (enclosed).

In the present invention, the method for the heat sealing treatment is not particularly limited, and any method known per se can be used. The methods for the heat sealing treatment is generally divided into rotary type heat sealing treatment, box motion type heat sealing treatment and reciprocation type heat sealing treatment, based on the movement of the main axis.

For formation of an embossed heat-sealed portion and a flat heat-sealed portion by a heat sealing treatment to package an adhesive preparation when, for example, the package is quadrangle, a conventional four side sealing packaging machine can be used.

One example of the method of packaging an adhesive preparation by rotary type heat sealing treatment using a conventional four side sealing packaging machine is as follows. Two long packaging films are set with the same sides facing each other, and an adhesive preparation is sandwiched between these packaging films from the above and below directions. Then, the both edges of the superimposed two packaging films are heat blocked in the longitudinal direction by applying heat. The heated both edges are pressed by a flat roll without concaves and convexes to perform a heat sealing treatment to form a flat heat-sealed portion. Then, a little outside of the formed flat heat-sealed portion is pressed with a roll having tatami-matting weave-like dots to form an embossed heat-sealed portion (whereby a heat-sealed portion is completed on both edges). Thereafter, a metal mold bar having a flat heat sealing surface, which is free of concaves and convexes, and a heat sealing surface having tatami-matting weave-like dots and the like in integrity is pressed in the direction perpendicular to the longitudinal direction of the packaging film such that a flat heat-sealed portion formed on the inside and an embossed heat-sealed portion formed on the outside to perform a heat sealing treatment, whereby a flat heat-sealed portion and an embossed heat-sealed portion are simultaneously formed (i.e., a heat-sealed portion perpendicular to the above-mentioned both edges is formed). Thereafter, it is cut into individual packages to give four side sealed packages.

One example of the method of packaging an adhesive preparation by a reciprocation type heat sealing treatment using a conventional four side sealing packaging machine is as follows. Two packaging films are set with the same sides facing each other, and an adhesive preparation is sandwiched between these packaging films from the above and below directions. Then, a heat block metal mold capable of forming heat-sealed portion simultaneously on four sides (having a flat heat sealing surface without concaves and convexes and a heat sealing surface having tatami-matting weave-like dots and the like) is heated, pressed against a packaging film for a heat sealing treatment to simultaneously form an embossed heat-sealed portion and a flat heat-sealed portion. Thereafter, a packaging film packaging the adhesive preparation is punched out with a cutting edge to give a four side sealed package. The box motion type sealing treatment includes a heat sealing treatment in the above-mentioned reciprocation type sealing treatment, which is performed while continuously transporting packages.

In the present invention, the box motion type sealing treatment and the reciprocation type sealing treatment are preferably used to prevent occurrence of pinholes as far as possible. When the adhesive preparation package is a quadrangle, a heat sealing treatment simultaneously forming the heat-sealed portion on four sides is most preferable.

In the adhesive preparation package of the present invention, for example, an adhesive preparation may be sandwiched between two packaging films, and the packaging film around the periphery of the adhesive preparation is heat-sealed to package (enclose) the adhesive preparation. Alternatively, one sheet of packaging film is folded into two, an adhesive preparation is sandwiched between them, the packaging film around the periphery of the adhesive preparation except the folded portion of the packaging film is heat-sealed to package (enclose) the adhesive preparation. However, since the position of the adhesive preparation during sandwiching between packaging films can be controlled with high precision, the adhesive preparation is preferably packaged (enclosed) using two packaging films.

While the conditions such as temperature, bonding pressure, pressure bonding time and the like in the above-mentioned heat sealing treatment vary depending on the constitution of a packaging film (e.g., thickness of packaging film, kind of thermal adhesive resin constituting the thermally adhesive resin layer and the like) and the like, they are appropriately set to afford desired band width and sealing strength. The temperature is generally within the range of 100° C. to 250° C. When the temperature is lower than 100° C., the thermally adhesive resin layer is not heat-sealed, and when the temperature is higher than 250° C., occurrence of wrinkles and foaming, deformation, degradation and the like of the base film constituting a packaging film causes poor appearance of the obtained package. The bonding pressure is generally 0.5 to 2.0 MPa, preferably 0.8 to 1.6 MPa, more preferably 0.9 to 1.5 MPa. When the bonding pressure is lower than 0.5 MPa, pinholes tend to occur and appropriate sealing strength cannot be obtained. When the bonding pressure is higher than 2.0 MPa, the packaging film easily breaks.

The packaging film in the adhesive preparation package of the present invention is not particularly limited as long as a heat-sealed portion is formed by a heat sealing treatment to enclose an adhesive preparation. It preferably has a base film layer and a thermally adhesive resin layer laminated on one surface of the base film. The packaging film may further have a dry laminate adhesive layer between a base film and a thermally adhesive resin layer to adhere them to each other. When a base film and a thermally adhesive resin layer are mutually adhered sufficiently by heat sealing, a dry laminate adhesive layer may not be formed.

As the base film layer, a resin film or sheet superior in transparency, which has superior mechanical, physical and chemical properties and other properties, particularly sufficient strength, toughness and heat resistance can be used. Specifically, a film, a sheet and the like of a strong resin, of, for example, polyester resin, polyamide resin, polyaramid resin, polyolefin resins such as polyethylene and polypropylene, polystyrene resin, polyacrylic, or polymethacrylic resin, polycarbonate resin, polyacetal resin, fluororesin, polyacrylonitrile resin, polyvinyl alcohol resin and the like can be used. As the above-mentioned resin film or sheet, a film stretched in a uniaxial direction of longitudinal direction or transverse direction can be used. As the stretching method, for example, known methods such as flat method, inflation method and the like can be used, wherein the draw ratio is about 2 to about 10. The thickness of the film is generally 5 μm to 100 μm, preferably 10 μm to 50 μm. In the present invention, the above-mentioned resin film may have, for example, a desired printed picture such as letter, graphic symbol, symbol, picture, pattern and the like by front printing, back printing and the like according to general printing methods.

As the dry laminate adhesive layer, generally employed dry laminate adhesives can be used, with preference given to those of a two component curing type adhesive. Particularly, polyester urethane polyol/aromatic polyisocyanate, polyetherpolyurethane/epoxy, polyetherurethane polyol/aliphatic polyisocyanate, polyester/aliphatic isocyanate and polyester/aromatic isocyanate are more preferable, and polyester urethane polyol/aromatic polyisocyanate is still more preferable. In addition, a suitable amount of any pigment or dye can be added to a dry laminate adhesive layer to color a packaging film.

The dry laminate adhesive layer can be formed by printing or coating a solution of a dry laminate adhesive on the surface of a base film layer or a thermally adhesive resin layer by gravure coating, roll coating, knife coating, spray coating, gravure printing, flexographic printing, screen printing, offset printing, other conventional printing or coating, and thereafter drying the printing or coating film. The thickness of the dry laminate adhesive layer is generally 1.0 g/m$^2$ to 30 g/m$^2$, preferably 2.0 g/m$^2$ to 20 g/m$^2$.

As the resin constituting the thermally adhesive resin layer, resins capable of melting and heat-sealing to each other by heat, and specifically, for example, resins such as polyolefin resins such as low density polyethylene, medium density polyethylene, high density polyethylene, linear low density polyethylene, polypropylene and the like; ethylene-vinyl acetate copolymer; ionomer resin; ethylene-acrylic acid copolymer; ethylene-ethyl acrylate copolymer; ethylene-methacrylic acid copolymer; ethylene-methyl methacrylate copolymer; ethylene-propylene copolymer; methylpentene polymer; polybutane polymer; acid-modified polyolefin resins obtained by modifying polyolefin resins such as polyethylene, polypropylene and the like with unsaturated carboxylic acids such as acrylic acid, methacrylic acid, maleic acid, fumaric acid, maleic anhydride and the like; vinyl polyacetate resin; poly(meth)acrylic resin; polyvinyl chloride resin; polystyrene resin; polyacrylonitrile resin; acrylonitrile-styrene copolymer (AS resin); acrylonitrile-butadiene-styrene copolymer (ABS resin); thermally adhesive polyethylene terephthalate; and the like can be used. The thermally adhesive resins most preferably used in the present invention are polyolefin resins such as low density polyethylene, medium density polyethylene, high density polyethylene, linear low density polyethylene, polypropylene and the like and polyacrylonitrile resins. A thermally adhesive resin layer can be constituted by a film or sheet of resins such as those mentioned above, or a coating film and the like of a resin composition containing a resin such as those mentioned above as a main component. The thickness thereof is generally 1 μm to 50 μm. For application to an adhesive preparation containing a drug, it is preferably 3 μm to 40 μm, more preferably 5 μm to 30 μm. When the thickness of the thermally adhesive resin layer is thinner than 1 μm, the heat sealability becomes poor and pinholes are easily produced. When the thickness is greater than 50 μm, the drug in the adhesive preparation transfers or adsorbs to the thermally adhesive resin layer in a greater proportion.

The packaging film of the present invention can have an intermediate base layer as necessary. As a base constituting the intermediate base layer, for example, a material impermeable to water vapor, water, gas and the like, or other materials can be used, which may be a single base member or a composite base containing two or more kinds of bases in combination and the like. Specifically, for example, a resin film having a vapor deposition film of inorganic oxide (e.g., silicon oxide, aluminum oxide etc.) having barrier property against water vapor, gas and the like, or a resin film or sheet of low density polyethylene, medium density polyethylene, high density polyethylene, linear low density polyethylene, polypropylene, ethylene-propylene copolymer and the like having barrier property against water vapor, water and the like, or a resin film or sheet of polyvinylidene chloride, polyvinyl alcohol, ethylene-vinyl acetate copolymer saponified product and the like having gas barrier property, or a resin film or aluminum foil and the like having an aluminum vapor deposition film can be used. These materials can be used alone or in a combination of two or more kinds thereof. While the thickness of the above-mentioned film or sheet may be any, it is generally 5 μm to 300 μm, preferably 10 μm to 100 μm. As the above-mentioned vapor deposition film of inorganic oxide, those having a thickness of 100 Å-3000 Å can be used. Moreover, as the above-mentioned aluminum vapor deposition film, those having a thickness of about 100 Å-400 Å can be used. As the resin film supporting the above-mentioned vapor deposition film, for example, polyester film, polyamide film, polyolefin film, polyvinyl chloride film, polycarbonate film, polyvinylidene chloride film, polyvinyl alcohol film, ethylene-vinyl acetate copolymer saponified product film and the like can be used. The thickness of the aluminum foil is preferably 3 to 30 μm, more preferably 5 to 10 μm. An adhesive preparation package having an aluminum vapor deposition film or a packaging film having an aluminum foil as an intermediate base layer does not permit clear identification of the adhesive preparation from the outside, thus making a check of an adhesive preparation in a package difficult, and further, visual inspection or image inspection of the presence of a pinhole in a flat heat-sealed portion difficult.

The packaging film in the present invention is preferably transparent, because a packaged adhesive preparation can be identified from the outside and the presence of a pinhole in a flat heat-sealed portion can be easily confirmed. Furthermore, since the heat-sealed portion of a packaging film and the portion free of heat sealing treatment can be certainly distinguished from each other based on the differences in the light transmittance and refractive index (formation state of the heat-sealed portion can be easily determined visually during the heat sealing treatment), a packaging film is preferably transparent. The flat heat-sealed portion has higher transparency than other portions, and therefore, when a flat sealed portion is formed without a pinhole, the flat sealed portion is considered to have been formed in a seamless manner. Moreover, the presence of a pinhole can be automatically checked by photographing the package with a camera and treating the images (binarization).

While the adhesive preparation of the present invention is not particularly limited, it preferably aims at treatment or prophylaxis of a disease by applying to the skin or mucous membranes and, more preferably, it comprises an adhesive layer, a support laminated on one surface of the adhesive layer and a peel-treated release liner laminated on the other surface of the adhesive layer. The adhesive layer may contain a transdermally absorbable drug.

As the adhesive constituting the adhesive layer, those adhered to the skin or mucous membrane for a certain time, such as those exhibiting adhesiveness in the ordinary state, those exhibiting adhesiveness under wet conditions, those exhibiting adhesiveness under heating and the like can be used. Specifically, water-soluble adhesive base mainly containing polyvinyl alcohol, polyvinylpyrrolidone, poly-N-vinylacetamide, polyethyleneoxide, polyacrylamide, polyacrylate, agar, xanthan gum and the like, water swellable adhesive base mainly containing a crosslinked water-soluble polymer, ethylcellulose, hydroxypropylcellulose, alginic acid ester and the like, and water-nonsoluble adhesive base mainly containing an acrylic polymer, a rubber polymer, a silicone polymer, a vinyl ether polymer, a vinyl ester polymer and the like can be used. These adhesives and adhesive bases may contain, where necessary, known additives such as tackifiers (e.g., rosin, modified rosin, petroleum resin, polyterpene resin, polystyrene resin, polybutane resin, liquid polyisobutylene, glycerin and the like), plasticizers (e.g., liquid paraffin, fatty acid ester and the like), absorption promoters, surfactants, fillers, water and the like, to further improve adhesiveness.

The thickness of the adhesive layer is generally 10 μm to 200 μm, preferably 15 μm to 150 μm.

The drug to be contained in the adhesive layer is not particularly limited as long as it is contained in an adhesive or adhesive base in a dissolution state, persaturation crystal precipitation state or dispersion state, and the adhesiveness of the adhesive or adhesive base can be retained. For example, corticosteroids, analgesic-antiphlogistic agent, sedative-hypnotic agent, ataractic, anti-hypertensive agent, hypotensive-diuretic, antibiotic, general anesthetic, antibacterial agent, antifungal agent, vitamin agent, coronary vasodilator, antihistamic agent, cough suppressant, sex hormone, antidepressant, cerebrovascular improver, antiemetic, antitumor agent, biological agent and the like can be mentioned.

While the content of the drug in the adhesive layer can be appropriately determined according to the kind of the drug, it is generally 1 wt % to 80 wt %, preferably about 2 wt % to 70 wt %. When the content is less than 1 wt %, a drug release in an amount effective for the treatment or prophylaxis cannot be expected, and when it exceeds 80 wt %, the adhesiveness is degraded to prevent sufficient adhesion. As a result, the effect of treatment or prophylaxis is limited and an economical disadvantage is produced.

The support layer is not particularly limited as long as the adhesion is not considerably uncomfortable. Specifically, a single film made from a synthetic resin such as polyester, polyolefin (e.g., polyethylene, polypropylene and the like), polyvinyl chloride, plasticized polyvinyl chloride, plasticized vinyl acetate-vinyl chloride copolymer, polyvinylidene chloride, ethylene-vinyl acetate copolymer, cellulose acetate, ethylcellulose, ethylene-ethyl acrylate copolymer, polytetrafluoroethylene, polyurethane, ionomer resin and the like, or a laminate film thereof, or a porous film or sheet, non-woven fabric or woven fabric made from rubber, the above-mentioned synthetic resins, polyesters such as polyethyleneterephthalate and the like or polyamides such as nylon and the like, or a laminate of these and the above-mentioned synthetic resin film, and the like can be mentioned. The thickness of the support layer is generally 1 μm to 1000 μm, preferably 1 μm to 100 μm for the above-mentioned single film or laminate film, and 100 μm to 1000 μm for the above-mentioned porous film or sheet, non-woven fabric, woven fabric and a laminate of these films. The material constituting the support layer in the present invention is not limited to the above-mentioned water insoluble materials and water-soluble materials such as polyvinyl alcohol, polyvinylpyrrolidone, poly-N-vinylacetamide, polyethyleneoxide, polyacrylamide, polyacrylate, agar, xanthan gum and the like may be used as long as they are non-toxic.

The exposed surface of an adhesive layer of the adhesive preparation of the present invention is preferably covered with a release liner to protect the surface until immediately before adhesion to the skin surface, so as to prevent unnecessary adhesion of the adhesive layer to instruments, containers and the like during production, unnecessary adhesion thereof to a packaging film during transportation or preservation, and degradation of an adhesive preparation. When in use, the release liner is peeled off to expose the surface of the adhesive layer, which is adhered to the object site for administration. The release liner is not particularly limited as long as it can be easily peeled off from the adhesive layer when in use and, for example, films of polyester, polyvinyl chloride, polyvinylidene chloride, polyethyleneterephthalate and the like, paper such as quality paper, glassine and the like, a laminate film of quality paper or glassine and the like with polyolefin and the like, after a peel treatment by applying silicone resin, fluorine resin and the like to the surface to be in contact with the adhesive layer, are used. The thickness of the release liner is generally 10 μm to 200 μm, preferably 50 μm to 100 μm.

The production method of the adhesive preparation used in the present invention is not particularly limited and, for example, a method comprising dissolving or dispersing a drug, an adhesive and the like in a solvent, applying the obtained solution or dispersion to one surface of a support, drying the support to form an adhesive layer on the surface of the support, and laminating a release liner on the adhesive layer and the like can be mentioned. Alternatively, the adhesive preparation can be produced by applying the above-mentioned solution or dispersion on a release liner for protection, drying the liner to form an adhesive layer on the release liner, and adhering a support to the adhesive layer.

The total thickness of the adhesive preparation to be packaged is within the range of 50 μm to 2000 μm, preferably 100 μm to 1000 μm. When the thickness of the adhesive preparation is less than 50 μm, an adhesive preparation can be packaged while suppressing the occurrence of pinholes even by a conventional heat sealing treatment, and therefore, the advantage afforded by the present invention is not very high.

When the thickness is greater than 2000 μm, the distortion of the packaging film due to the thickness cannot be suppressed by a flat heat-sealed portion, and pinholes easily occur.

EXAMPLES

The present invention is explained in detail by referring to Examples, which are not to be construed as limitative.

Example 1

Using a laminate film of a packaging film: transparent polyethyleneterephthalate film (thickness: about 12 μm)/polyacrylonitrile resin film (product name: HIGHTORON BX, manufactured by TAMAPOLY CO., LTD., thickness: about 20 μm), an adhesive preparation (thickness: 680 μm, size: 50×30.5 mm) containing lidocain as a transdermally absorptive drug was packaged (enclosed) by a heat sealing treatment under the following conditions to give an adhesive preparation package having the form shown in FIG. 1.

The size of package: 50 mm×70 mm rectangle, band width of flat heat-sealed portion: 0.5 mm, band width of embossed heat-sealed portion: 5 mm, concave-convex pattern of embossed heat-sealed portion: 0.6 mm pitch tatami-matting weave-like dots, heat sealing treatment method: reciprocation type sealing treatment using a four side seal packaging machine for simultaneous heat sealing treatment of the four sides with a metal mold, heat sealing treatment temperature: 180° C., heat sealing treatment pressure: 0.9 MPa.

Example 2

Using a laminate film of a packaging film: transparent polyethyleneterephthalate film (thickness: about 16 μm)/polyethylene resin film (manufactured by Kaito Chemical Industry Co., Ltd., thickness: about 40 μm), an adhesive preparation (thickness: 140 μm, size: 63.5 mm×63.5 mm) containing isosorbide dinitrate (ISDN) as a transdermally absorptive drug was packaged (enclosed) by a heat sealing treatment under the following conditions to give an adhesive preparation package having the form shown in FIG. 1.

The size of package: 85 mm×85 mm square, band width of flat heat-sealed portion: 1.0 mm, band width of embossed heat-sealed portion: 7 mm, concave-convex pattern of embossed heat-sealed portion: 7 mm pitch tatami-matting weave-like dots, heat sealing treatment method: reciprocation type sealing treatment using a four side seal packaging machine for simultaneous heat sealing treatment of the four sides with a metal mold, heat sealing treatment temperature: 140° C., heat sealing treatment pressure: 1.0 MPa.

Comparative Example 1

In the same manner as in Example 1 except that a flat heat-sealed portion was not formed, and the heat sealing treatment was performed by a rotary type sealing treatment, an adhesive preparation package was obtained.

Comparative Example 2

In the same manner as in Example 2 except that a flat heat-sealed portion was not formed, and the heat sealing treatment was performed by a rotary type sealing treatment, an adhesive preparation package was obtained.

Comparative Example 3

In the same manner as in Example 1 except that an embossed heat-sealed portion was not formed, and the band width of the flat heat-sealed portion was 5.5 mm, an adhesive preparation package was obtained.

Comparative Example 4

In the same manner as in Example 1 except that a flat heat-sealed portion was not formed, an adhesive preparation package was obtained.

The adhesive preparation packages obtained in Examples 1, 2 and Comparative Examples 1 to 4 were subjected to the following test, and the properties of the adhesive preparation packages were compared. The results are shown in the following Table 1.

(Sealing Strength of Package)

The sealing strength of the package was measured according to the heat sealing test method of bag as defined in JIS Z0238 "Test Method of Concealed Soft Packaging Bag".

(Confirmation of Pinholes)

Confirmation of the presence of a pinhole in the heat-sealed portion of a package followed leak test method A as defined in JIS Z0238 "Test Method of Concealed Soft Packaging Bag". In the test, 20 packages were randomly selected from plural packages, and the number of packages that showed infiltration of a test solution due to a pinhole was counted for evaluation.

(Appearance)

The 20 packages randomly selected from plural packages were visually confirmed for the appearance of the entire package and a heat-sealed portion, as well as the presence of wrinkles and pinholes. The number of the package in the 20 packages, which showed poor appearance, was evaluated.

TABLE 1

| | Seal strength (N/15 mm) | Confirmation of pinholes (number of packages/ number of packages) | Appearance | Poor appearance (number of packages/ number of packages) |
|---|---|---|---|---|
| Ex. 1 | 11.5 | 0/20 | No wrinkles and no pinholes, good appearance | 0/20 |
| Ex. 2 | 28.0 | 0/20 | No wrinkles and no pinholes, good appearance | 0/20 |
| Com. Ex. 1 | 6.5 | 15/20 | Wrinkles and pinholes in sealed portion | 13/20 |
| Com. Ex. 2 | 15.5 | 3/20 | No wrinkles, good appearance | 0/20 |
| Com. Ex. 3 | 7.5 | 4/20 | Wrinkles and pinholes in sealed portion | 20/20 |
| Com. Ex. 4 | 10.5 | 17/20 | No wrinkles, good appearance | 0/20 |

From the results of Table 1, the package of Examples 1 and 2 having a flat heat-sealed portion were easily confirmed to be free of a pinhole by visual observation of the appearance. In addition, the absence of a pinhole was also confirmed by the leak test.

In contrast, the package of Comparative Example 1 was confirmed to have wrinkles and pinholes by visual observation of the appearance, and the presence of pinhole was confirmed by the leak test. The package of Comparative Example 2 showed fine results by visual observation of the appearance but 3 out of 20 showed liquid leakage by the leak test and the presence of pinhole was confirmed. The package of Comparative Example 3 was confirmed to have wrinkles and pinholes by visual observation of the appearance, and the presence of pinhole was also confirmed by the leak test. The package of Comparative Example 4 showed fine results by visual observation of the appearance but 17 out of 20 showed liquid leakage by the leak test and incomplete enclosing was confirmed.

This application is based on patent application Nos. 195321/2004 and 172516/2005 filed in Japan, the contents of which are hereby incorporated by reference.

The invention claimed is:

1. An adhesive preparation package comprising an adhesive preparation and at least one packaging film enclosing said preparation, the packaging films being heat-sealed around the adhesive preparation, wherein
   the heat-sealed portion of the packaging film comprises an embossed heat-sealed portion and a flat heat-sealed portion, and
   both the embossed heat-sealed portion and the flat heat-sealed portion each singly form a pattern surrounding the periphery of the adhesive preparation, wherein the pattern is, in the order from the inside, selected from the group consisting of
   (1) a flat heat-sealed portion and an embossed heat-sealed portion,
   (2) an embossed heat-sealed portion, a flat heat-sealed portion, and an embossed heat-sealed portion, and
   (3) a flat heat-sealed portion, an embossed heat-sealed portion, and a flat heat-sealed portion.

2. The adhesive preparation package of claim 1, wherein the flat heat-sealed portion has a band width of 0.4 mm to 2.0 mm.

3. The adhesive preparation package of claim 1, wherein the embossed heat-sealed portion and the flat heat-sealed portion each form a pattern concentrically surrounding the periphery of the adhesive preparation.

4. The adhesive preparation package of claim 1, wherein the heat-sealed portion of the at least one packaging film has a total band width of 3 mm to 20 mm for the combination of the embossed heat-sealed portion and the flat heat-sealed portion.

5. The adhesive preparation package of claim 1, wherein the adhesive preparation is sandwiched between two packaging films, and the packaging films around the periphery of the adhesive preparation are heat-sealed.

6. The adhesive preparation package of claim 1, wherein the adhesive preparation has a thickness of 50 μm to 2000 μm.

7. The adhesive preparation package of claim 1, wherein the adhesive preparation comprises an adhesive layer, a support laminated on one surface of the adhesive layer and a peel-treated release liner laminated on the other surface of the adhesive layer.

8. The adhesive preparation package of claim 7, wherein the adhesive layer comprises a transdermally absorbable drug.

9. The adhesive preparation package of claim 1, wherein the packaging film comprises a base film layer and a thermally adhesive resin layer having a thickness of 3 μm to 40 μm is laminated.

10. The adhesive preparation package of claim 9, wherein the resin constituting the thermally adhesive resin layer is a polyacrylonitrile resin or a polyolefin resin.

11. The adhesive preparation package of claim 1, wherein the packaging film is transparent.

* * * * *